United States Patent [19]
Gianotti et al.

[11] Patent Number: 5,626,602
[45] Date of Patent: May 6, 1997

[54] CATHETER WITH A VASCULAR SUPPORT

[75] Inventors: Marc Gianotti, Wiesendangen; Paul Lehmann, Winterthur, both of Switzerland

[73] Assignee: Schneider (Europe) A.G., Bulach, Switzerland

[21] Appl. No.: 375,591

[22] Filed: Jan. 17, 1995

Related U.S. Application Data

[62] Division of Ser. No. 97,799, Jul. 27, 1993, Pat. No. 5,405,380.

[30] Foreign Application Priority Data

Oct. 12, 1992 [EP] European Pat. Off. ............ 92203134.9

[51] Int. Cl.⁶ .................................................. A61M 29/00
[52] U.S. Cl. ........................................ 606/198; 606/191
[58] Field of Search .................... 606/1, 191, 198, 606/108; 623/1, 11, 12; 604/164, 764, 96–104

[56] References Cited

U.S. PATENT DOCUMENTS

| | | | |
|---|---|---|---|
| 4,655,771 | 4/1987 | Wallsten | 623/1 |
| 4,665,918 | 5/1987 | Garza et al. | 128/343 |
| 4,732,152 | 3/1988 | Wallsten et al. | 128/343 |
| 4,848,343 | 7/1989 | Wallsten et al. | 128/343 |
| 4,875,480 | 10/1989 | Imbert | 128/343 |
| 4,885,003 | 12/1989 | Hillstead | 604/22 |
| 4,921,484 | 5/1990 | Hillstead | 604/104 |
| 4,950,227 | 8/1990 | Savin et al. | 604/8 |
| 4,990,151 | 2/1991 | Wallsten | 606/108 |
| 5,002,560 | 3/1991 | Machold et al. | 606/198 |
| 5,034,001 | 7/1991 | Garrison et al. | 604/53 |
| 5,071,407 | 12/1991 | Termin et al. | 604/104 |
| 5,108,416 | 4/1992 | Ryan et al. | 606/194 |
| 5,158,548 | 10/1992 | Lau et al. | 604/96 |
| 5,180,368 | 1/1993 | Garrison | 604/104 |
| 5,190,058 | 3/1993 | Jones et al. | 128/898 |
| 5,192,297 | 3/1993 | Hull | 606/195 |
| 5,201,757 | 4/1993 | Heyn et al. | 606/198 |
| 5,221,261 | 6/1993 | Termin et al. | 604/104 |
| 5,449,372 | 9/1995 | Schmaltz et al. | 606/198 |

FOREIGN PATENT DOCUMENTS

| | | |
|---|---|---|
| 321912A1 | 6/1989 | European Pat. Off. . |
| 408245A1 | 1/1991 | European Pat. Off. . |
| 418677A1 | 3/1991 | European Pat. Off. . |
| 423916A1 | 4/1991 | European Pat. Off. . |
| 433447A1 | 6/1991 | European Pat. Off. . |
| 1250058 | 9/1967 | Germany . |
| 9107928 | 6/1991 | WIPO . |

*Primary Examiner*—Glenn Dawson
*Attorney, Agent, or Firm*—Lawrence C. Akers; Peter C. Richardson; Philip C. Strassburger

[57] ABSTRACT

A catheter with a radially self-expanding cylindrical vascular support made of a permeable mesh of crossed stiff fibers is disclosed. The catheter has a tubular outer catheter shaft and an inner catheter to which the vascular support is fixed. The tubular outer catheter shaft is axially movable with respect to the inner catheter.

2 Claims, 2 Drawing Sheets

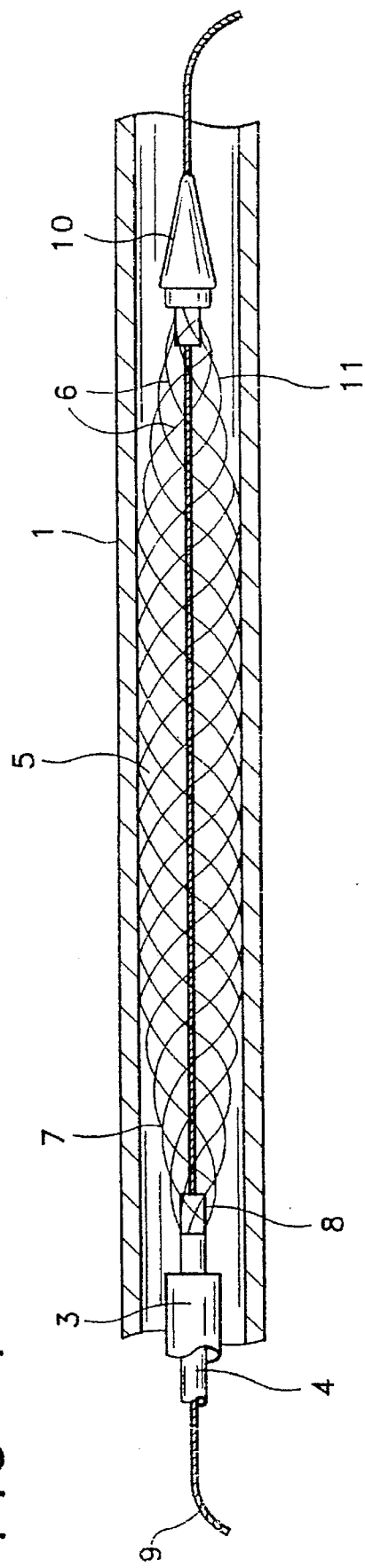
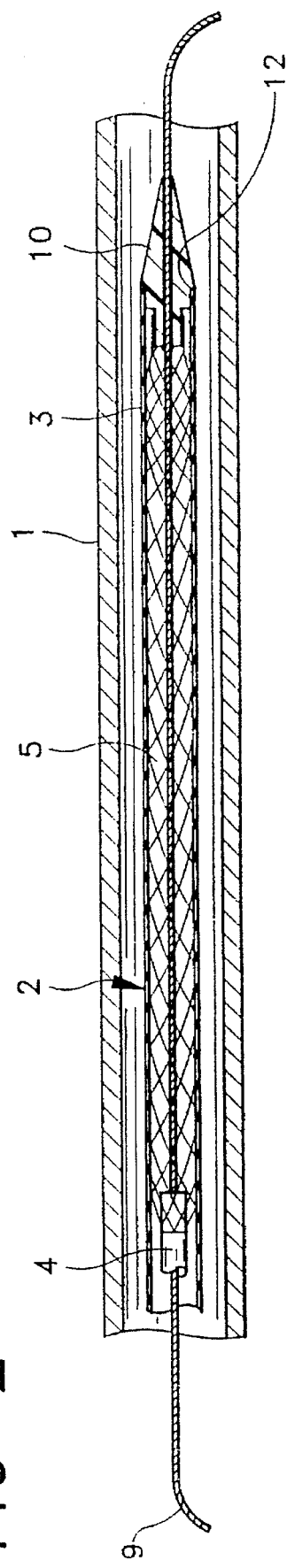

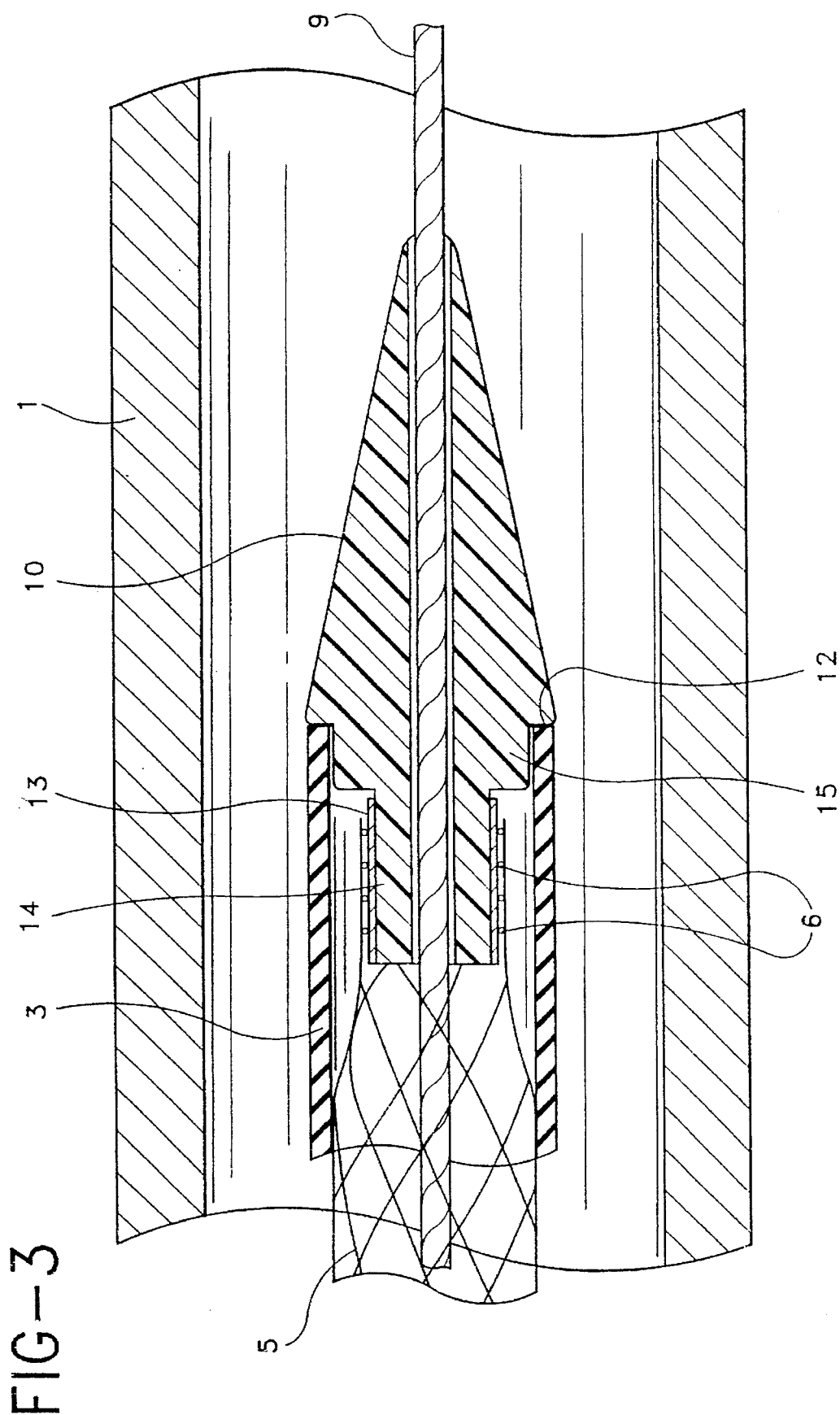

5,626,602

CATHETER WITH A VASCULAR SUPPORT

This is a division of application Ser. No. 08/097,799, filed on Jul. 27, 1993 now U.S. Pat. No. 5,405,380.

BACKGROUND OF THE INVENTION

The invention relates to a catheter: with a cylindrical vascular support made of a permeable mesh of crossed stiff fibers, in which the vascular support, when inserted, expands on its own by means of its radial elasticity from a taut state with a small circumference into a relaxed state supporting the vascular wall with a consistent circumference over the entire length; with a tubular outer catheter shaft which receives the taut vascular support at its distal end and from which the vascular support can be released for insertion; and with an inner catheter inside the tubular outer catheter shaft which can be slid within the outer catheter, which is supported along its length for direct conveyance of the sliding routes in the outer catheter and which leaves a passage free in its interior for a guide wire, which it tightly encloses; in which the outer catheter shaft is drawn back with respect to the inner catheter to release the vascular support; in which the vascular support is secured at its proximal end when clamped in such a way that it forms, together with the vascular support, a self-opening permeable mesh cone, the radius of which steadily increases to the size of the radius of the relaxed vascular support; and in which the vascular support, with the aid of the mesh cone, is firmly anchored to the inner catheter, which transmits only compressive and tensional forces.

Catheters of this type have a vascular support at their distal end which is only inserted into the body temporarily in order to support a vascular wall during a specific period of time. After that, the vascular support is to be removed from the vessel.

Vascular wall supports that remain permanently in the body are used, for example, after balloon dilation of a coronary vessel. A main complication in this technique consists of the fact that, as a result of the forcible expansion of the blood vessel, part of the intima, the innermost layer of the vascular wall, can separate from the vascular wall and can then hinder the flow in the vessel to a greater or lesser extent. In the worst case, a separated section of the vascular wall can act like a valve flap, which completely blocks the flow. At specific treatment sites, for example, precisely in the coronary arteries, this leads to a critical situation, which makes an emergency bypass operation necessary with high risk to the patient. However, even at other treatment sites and in the case of a less unfavorable course of complication, this effect, at any rate, prevents the success one seeks to achieve with the treatment.

For some time, therefore, in the case of such complications, the vascular support known from U.S. Pat. No. 4,655,771, for example, have been inserted into the vessel at the site to be treated in order to keep the vessel open from the inside.

For this purpose, using the same puncture that has already been used for the balloon catheter, a catheter is introduced into the blood vessel. The vascular support is cylindrical and consists of a mesh of crossed stiff fibers. It is self-expanding, i.e., it is inserted into the catheter in the taut state and then relaxes on its own without assistance. Other types of vascular supports have to be expanded, e.g., by means of an internal balloon. At the treatment site, the vascular support is released and separated from the catheter by drawing back the outer catheter. A sliding inner catheter located within the catheter serves as a support for the vascular support while the outer catheter is pulled back. After its release, the vascular support remains in the vessel and supports the vessel permanently. The catheter, on the other hand, is withdrawn in the usual manner and the vessel puncture site is closed.

Vascular supports of this type fulfill their purpose to the extent that they press the separated, innermost vascular layer, the intima, back against the vascular wall and thus keep the vessel open for flow. However, problems arise insofar as these vascular supports can cause blood clots, since they represent foreign bodies in the vessel. This danger must be counteracted with high, potentially dangerous doses of anticoagulant agents. After several weeks, the vascular support is then overgrown by the inner skin of the vessel, the endothelium, and the danger of blood clots is thereby largely averted. Now a new problem arises. This is namely because the tissue cells, the growth of which was stimulated by the introduction of the vascular support, do not stop growing in some cases. A new partial or complete occlusion of the vessel can therefore occur.

However, it has become known in the meantime that a separated intima can be reconnected to the vascular wall and healed within a relatively short time. In some cases, all that is required is another brief filling of the balloon at the end of the balloon catheter described. While the balloon is stretched, however, blood flow is interrupted in the vessel in question. This method therefore cannot be used at all treatment sites. In addition, the healing times are prolonged by anticoagulant drugs that may be necessary during the treatment. In this case, the blood supply would accordingly have to be interrupted for a longer period if one wanted to press the intima against the vessel wall by means of a balloon.

In order to avoid the problems described, catheters have therefore already been proposed in which the vascular support can be removed from the vessel. In this case, no implant remains in the body and the complications related to this do not occur. As soon as the vascular support has fulfilled its task and the intima has been reconnected to the vascular wall, this aid can be removed from the body.

An example of this is described in European patent application 0 321 912 A1. It involves a vascular support consisting of a longitudinally stretched mesh tubing made of interwoven wires which is introduced into the vessel in its stretched state. At the treatment site, the two ends of the mesh tube are moved towards each other. As a result, the mesh between the ends bulges into a hollow form which lays against the inner wall of the vessel and supports it. The mesh from which the vascular support is made thus is not self-expanding in this case, but rather is relaxed in the stretched state. In this relaxed stretched state with a small circumference, the vascular support is introduced into the vessel and is then removed from the vessel after use. The strength of the pressure the hollow form exerts on the vascular wall depends on the degree of force with which the ends of the mesh tube are moved towards each other. However, a disadvantage of this design is that the individual wires can kink if the ends of the mesh tube are drawn toward each other with too much force, and the wires cannot move out of the way in the vessel. With kinked wires, the catheter can be removed from the vessel only with complications, because the actuating elements of the mesh can transmit compressive forces only to a limited extent in order to return the mesh to its stretched state with a small circumference. Another disadvantage is the fact that the actuating forces for keeping the mesh tube open for the length of treatment must be maintained from the outside over a relatively long distance. In this case, transmission failures can occur if, for example, the catheter is moved between the skin puncture and the treatment site.

Another example for a vascular support that can be removed from the body is shown in World Patent Application 91/07 928. In this case, the vascular support is made from a helically wound single wire. The wire is inserted stretched into a thin catheter tube and is pushed forward out of this. As soon as the wire emerges from the front of the thin catheter tube, it takes on a spiral or helical form, because of its designed tension. The individual turns of the helical form push outward radially and support the vascular wall. To remove the vascular support, the wire is drawn back into the catheter. In this process, the wire again reassumes its stretched form. This vascular support is therefore self-expanding. With the self-expanding type of vascular supports there is no threat of the danger that excessive operating forces will impair the vascular support or make it unusable. However, the use of only a single wire is accompanied by the disadvantage that the individual turns of the vascular support must be arranged very close together in order to support the surface of the vascular wall and therefore be effective. In addition, in a helical form with only one wire, the turns are not connected to each other, so that there is nothing to keep the distance between the turns uniformly close. Gaps in the support of the vascular wall can thus develop. Another unpleasant disadvantage is the fact that the helical vascular support does not remain stationary during insertion and removal from the vessel. During the insertion and removal of the vascular support, each relaxed part of the helical spring must rotate with respect to the wire in the catheter in order to compensate for the different state of the wire. During placement of the vascular support, the free, rotating end of the wire can cause damage to the vascular wall in this process. Primarily, however, during insertion, the helical vascular support can move below a separated flap of the vascular wall as a result of its rotation and can thus prevent the fulfillment of its task. The action of this vascular support is therefore not as reliable as, for example, that of the known vascular support that remains permanently in the vessel. Problems can also result from the fact that, at the proximal end of the catheter, the total force for ejecting the vascular support must be transmitted by means of only one wire.

Another example of a vascular support that can be removed from the vessel has been published in European Patent Application 0 423 916 A1. This involves a slidable screen made of stainless steel wire and assembled in the form of a section of tube jacket. This vascular support is also self-expanding and, just like the vascular support according to U.S. Pat. No. 4,655,771, is inserted into the vessel by drawing back an outer catheter with respect to an inner catheter. At the close, proximal edge of the slidable screen that has been assembled into a tube jacket section a thread is attached at the edge of the tube jacket. With this thread, the tube jacket can be tied together at its proximal end. In order to achieve this, both ends of the thread are guided out of the body and are loosely secured there while the vascular support is in the vessel. If the vascular support is to be removed, a new catheter is fed over these two threads up to the vascular support and the proximal end of the support is tied together by pulling on the threads. Then a second, correspondingly larger catheter is pushed over the first. The vascular support is now pulled together with the threads far enough until it fits into the larger catheter and can be drawn into it. After this, both catheters, together with the vascular support, are removed. The disadvantage of this arrangement is the large effort it requires. The operation is very cumbersome because of the handling of the threads and the placement of at least one new catheter, which, for example, must also be pushed over the threads. A large number of instruments is also required, and at least one additional catheter must be provided that will receive the vascular support. The catheter used for placement of the vascular support is too small for this purpose. In inserting the vascular support into the coronary arteries, difficulties are also to be expected when drawing the vascular support into the larger catheter, because the coronary arteries are in constant movement. The difficulties then arise due to the fact that the vascular support, which is drawn together at the proximal end, does not always lie exactly in the center of the larger catheter and the vascular support also does not center itself with respect to the larger catheter. The vascular support remains hanging at the edge of the larger catheter.

The catheter with a vascular support, constituting the preamble of the claim, became known after the filing date of European Patent Application 92 200 294.4 and corresponds to the description given there.

In this catheter, a self-expanding vascular support according to U.S. Pat. No. 4,655,771, made of a permeable mesh of crossed fibers is anchored in a folded and inserted state to an inner catheter at the proximal ends of the mesh fibers. While the catheter is fed into the vessel, the vascular support is supported in the inserted state in a corresponding outer catheter. As soon as the outer catheter is withdrawn with respect to the inner catheter, the vascular support will emerge distally from the outer catheter and relax. Due to the fact that it is anchored to the inner catheter in a folded state, a mesh cone is formed at the proximal end of the vascular support in the relaxed state. The conical form of the mesh and its anchoring to the inner catheter make it possible for the vascular support to be reliably folded back into the outer catheter after use by advancing the outer catheter and thus to remove it from the vessel.

This catheter corresponds largely to the demands made on it, but a still unsatisfactory factor with regard to this catheter is the phase during the course of the operation where the taut vascular support is located within the outer catheter and the catheter is fed into the vessel. In this phase, the outer catheter must be closed by means of a protective cap. Otherwise, the outer catheter would load up with the respective body fluid when it was fed into the vessel. Primarily, the vascular wall would then be directly exposed to the advancing edge of the distal outer catheter opening. Injuries can be caused as a result. To prevent injuries in general when feeding a catheter into a vessel, a guide wire is normally inserted, which guides the catheter from the inside and over which the catheter is advanced. In the catheter under discussion in the present case, the insertion of a guide wire cannot permanently eliminate the danger of injury. On the one hand, a guide wire must be as thin and flexible as possible and, in any case, the possibility of injuries caused by the guide wire itself must be ruled out with certainty. The distal opening of the outer catheter, through which the guide wire rubs, on the other hand, must be many times larger than the diameter of the guide wire, because it must receive the vascular support. Because of the large difference in diameter between the guiding element on the one hand and the element to be guided on the other hand, a guide wire cannot conduct this catheter with the required safety and thus prevent the possibility of injuries. The protective cap, which is provided at the distal end of the catheter, also presents problems. On the one hand, it should close the distal outer catheter opening reliably in the closed state and protect the vascular wall reliably against injuries. On the other hand, however, it should, if possible, not offer any resistance to the withdrawal and the folding in of the vascular support. It is difficult to satisfy both requirements at the same time. Primarily, however, difficulties are to be expected in folding the vascular support back into the outer catheter in the case of vascular supports made from a wide mesh net. In addition to the tasks described above, the protective cap cannot also guide the catheter along the guide wire. This would contradict the requirement that the cap must also permit easy withdrawal of the vascular support. The guide wire in this catheter therefore has practically no perceptible guidance and is uncontrolled in the much larger distal opening of the outer catheter.

SUMMARY OF THE INVENTION

The invention has therefore taken on the task of providing a catheter with a vascular support which can be reliably removed from the vessel after a temporary period of use, which can be advanced reliably along a guide wire, which does not collect any vascular fluid when fed into the vessel, and which prevents injuries to the vascular wall caused by the edge of the distal catheter opening.

This problem is solved by the fact that the stiff fibers that form the mesh are brought together again at their ends and are anchored distally to a tip, thereby forming a second mesh cone, which is a mirror image of the first, at the distal end of the vascular support, where the guide wire passes through the inside of the tip to which the fibers are anchored and its exterior is formed in such a way that it closes the distal opening of the outer catheter when the outer catheter receives the completely taut vascular support, and where the tip, when it closes the outer catheter, extends distally, with its distal end tapering with respect to the distal opening of the outer catheter to such an extent that the full outside diameter of the catheter cannot hit the vascular wall at an obtuse angle. The tip at which the distal ends of the fibers are anchored thus takes on the functions of the protective cap of the known catheter. It represents a closure preventing the outer catheter from becoming filled with body fluids when fed into the vessel or perhaps from slipping off and collecting deposits from the vascular walls. However, the closure in this case is not fastened to the outside catheter, as in the state-of-the-art type, but rather to the vascular support and, specifically, to its distal end. As a result, it moves together with the vascular support and then automatically closes the distal outer catheter opening as soon as the vascular support is withdrawn with respect to the outer catheter. In contrast to the protective cap, the tip does not oppose the free unfolding and folding back of the vascular support, and in this arrangement, there is no longer any contradiction between the requirements for a reliable closure with good protection against injury on the one hand and, on the other hand, a secure release and reliable folding together of the vascular support. At the same time, the tip also takes on the guidance forces from the guide wire because it receives the guide wire. It transmits the guidance forces to the catheter and thereby ensures a satisfactory, reliable operation of the catheter along the guide wire. The catheter can be advanced blindly, rapidly, reliably, and without danger of injury along the guide wire. As a result of the fact that the tip extends distally in a tapered manner so far with respect to the opening of the outer catheter that the full outer catheter cannot hit the vascular wall at an obtuse angle, the tip prevents possible injuries of the vascular wall by the catheter when advanced. The vascular wall is no longer exposed unprotected to the relatively thin and thus potentially traumatic, injuring outer catheter edge. Finally, as a result of the tip, danger of injury by the distal ends of the vascular support is also eliminated. This is because when the known, distally open vascular support is fed into the vessel, the distal ends of the vascular-support fibers spread apart and bore in an outward direction into the vascular wall. It is, of course, unlikely that the vascular support will be inadvertently advanced during operation, which would also be a major misoperation of the catheter because the vascular support would be compressed as a result and the fibers of the vascular support could become kinked. While the vascular support is being used, however, the entire remaining length of the catheter is still located in the patient's body. The danger of injury then results less from possible improper operation of the catheter than from possible, perhaps unavoidable, movements of the patient. The patient's movement can be transmitted to the inner catheter and can thereby also exert pressure on the vascular support. The tip provided in the invention, which consolidates all the distal ends of the vascular-support fibers into itself and secures them, now permanently prevents any danger of injury to the patient in this case as well.

If the tips have a shoulder overlapping the outer catheter, this enables the distal opening to be sealed particularly well. In advancing the outer catheter, it will be a distinctly perceptible when the vascular support has completely folded in again. In this case, the tip can also serve simultaneously as a dilator in narrow vascular passages and in the introduction of the instrument at the puncture site. The cost of a special insertion set and the time spent in manipulating it are saved. In emergency situations, this is a point of particular interest.

Because the tip can be detected radiologically, the position of the distal end of the vascular support can also be checked by X-rays, without the need to use special radio-opaque material for the vascular-support fibers. In that case, the physician has precise control of the distal end of the support as well, even after the vascular support has already been put in place. He can then precisely evaluate any possible misplacements or displacements and, if necessary, correct them.

A particularly advantageous arrangement is obtained if a radio-opaque ring is attached to the tip, to which the distal ends of the vascular support fibers are anchored. By combining two functions in one, these measures result in a simple tip form and an instrument that can be easily and simply installed. The radio-opaque ring in this arrangement does not disturb the outside surface that comes into contact with the vascular wall and also does not interfere with any other functions of the tip.

A particularly advantageous process for producing a catheter according to the invention is obtained if the converging ends of the two mesh cones of the vascular support are each held closed by a tube shrunk on the outside diameter of the corresponding anchoring base on the inner catheter or on the tip, while the mesh cones are connected to the inner catheter or to the tip. As a result of this, by means of a simple step, the mesh of the vascular support is clamped down uniformly on all sides and the connection can be made without any problems by means of heat treatment or by using bonding agents. However, a particular advantage of this method is also the fact that the clamping exerts a constant force, even if the clamped object yields or even becomes smaller in diameter. This characteristic of the proposed process is important if the connection is to be made by heat treatment, but also if the smallest possible diameter of the finished connection is to be achieved when the connection is made using bonding agents.

By means of this process, therefore, a catheter with a particularly small outer diameter can be produced.

BRIEF DESCRIPTION OF THE DRAWINGS

The invention will be explained in greater detail below using the design examples in the drawings:

FIG. 1—a view of the catheter according to the invention with the released vascular support in a schematically indicated vessel.

FIG. 2—a longitudinal section through a catheter according to the invention with a clamped vascular support.

FIG. 3—a detail of a longitudinal section through an example of a different design of a catheter according to the invention with a clamped vascular support.

DETAILED DESCRIPTION OF THE INVENTION

In FIG. 1, 1 is an ideal representation of a vessel from the body of a human, for example. The vessel can take in fluids, e.g., blood, but it can also conduct air, so that the vessel can also represent an air tube. Located in this vessel is the far, distal end of catheter 2. Catheter 2 has been inserted into the vessel at a suitable spot, e.g., at a puncture site, and has been fed from outside the body up to the point in the vessel shown. Catheter 2 consists of a tubular outer catheter shaft 3 and a sliding inner catheter 4 located inside this. Inner catheter 4 is supported along its length in outer catheter 3 just tightly enough that longitudinal movement of the inner catheter inside the outer catheter will not require any forces that no longer permit sensitive operation. The sliding routes at the close, proximal side are therefore conveyed without hysteresis phenomena to the distal working end of inner catheter 4. In the position shown in FIG. 1, inner catheter 4 has been pushed out to a certain distance from the distal end of outer catheter shaft 3.

On the inside, inner catheter 4 tightly encloses a passage for guide wire 9.

A guide wire is a wire that is designed to be so flexible that injuries to the vessel caused by the wire when it is advanced are eliminated. A guide wire is used, in any case, at the site where the vessel is punctured. Using the "Seldinger Technique," after puncture with a hollow needle, a guide wire is first inserted into the vessel through the hollow needle at that site. Then, for example, a dilator of an insertion set is advanced over the guide wire. The dilator widens the puncture site, for example, for a hollow catheter called an "insertion shunt," which is pushed directly over the dilator. After the dilator has been removed, the various catheters can then be inserted into the vessel through the insertion shunt, primarily including those without a dilator at their distal end and those without a central passage or without a central lumen for a guide wire.

Inner catheter 4 encloses the passage for guide wire 9 just tightly enough that the guide wire can still move readily with respect to the inner catheter. This enables small overall dimensions for the catheter tube. This is desired so that when the vascular support 5 is inserted, the medium flowing in vessel 1 is hindered as little as possible by catheter 2.

Wire 9 can also be a guide wire that is used not only at the puncture site, but rather in general is fed in to insert catheter 2 into the body and catheter 2 then follows it. However, it can also be a guide wire from a previous treatment that has already been fed in up to the treatment site in the body and is still located there, for example, from treatment with a balloon catheter.

Vascular support 5 is also shown in vessel 1. Vascular support 5 is made of a permeable mesh of crossed stiff fibers 6. The stiffness of fibers 6 and the process for the producing the mesh are selected in such a way that vascular support 5, when inserted, expands on its own by means of its radial elasticity from a taut state with a small diameter to a relaxed state supporting the vascular wall, with a consistent circumference constant over its length.

Stiff fibers 6 that form the mesh are helically placed and crossed over one another. They thus form a specific angle to the longitudinal axis of he vessel and can, for example, through their spiral form, support themselves at each opposite vascular wall. As a result of this, a relatively high contact pressure is achieved, but above all one that remains constant over the length of the fiber and over the length of the vascular support. Fibers without a helical form can support only at their respective root and end points, whereas, at the midpoint between these support points, the support pressure they exert on the vascular wall decreases once they no longer rest against the vascular wall in a punctiform manner but rather over a specific vascular length.

FIG. 2 shows vascular support 5 in the taut state. Vascular support 5, constricted to a small circumference, is mounted at the distal end of tubular outer catheter shaft 3. In order to open vascular support 5 and to release it for use in the relaxed state in which it self-expands, rests against the vascular wall and supports the latter, outer catheter shaft 3 is drawn back with respect to inner catheter 4.

If outer catheter 3 is drawn back with respect to the inner catheter, then inner catheter 4 must axially support at its proximal end vascular support 5, which rests against the inner wall of outer catheter shaft 3, so that relative movement between outer catheter shaft 3 and vascular support 5 can occur.

It can be seen particularly in FIG. 1 that the vascular support, clamped at its close, proximal end, is secured in such a way that it forms permeable mesh cone 7. Mesh cone 7 is made of the same stiff fibers 6 that also form vascular support 5, so that cone 7 opens together with the vascular support itself. The radius of this mesh cone 7 increases steadily until it reaches the radius of vascular support 5. At its tip, mesh cone 7 is constricted to the outer diameter of inner catheter 4. At this point, it is connected to the inner catheter by a layer of bonding agent. Vascular support 5 is therefore anchored firmly to the inner catheter at connection point 8 by means of mesh cone 7.

Inner catheter 4 only has to transmit compressive and tensional forces for opening and closing vascular support 5. Its wall thickness can therefore be kept very low. This also leads to small outside dimensions of catheter 2, which cause little interference with the media flow in the vessel. The other ends of stiff fibers 6, after they have formed vascular support 5, are brought together again and are anchored distally at tip 10. As a result, at their distal end, these fibers form a second mesh cone 11, which is a mirror image of the first.

Tip 10 to which fibers 6 are anchored is shown in FIG. 2. In its interior, it permits passage of guide wire 9. Guide wire 9 can move freely with respect to tip 10, so that tip 10 can freely change its position with respect to the distal end of inner catheter 3 during opening and closing of the vascular support and guide wire 9 can be moved independently of catheter 2. At the same time, the passage for guide wire 9 through tip 10 centers guide wire 9 with respect to catheter 2.

In the position of vascular support 5 shown in FIG. 2, in which outer catheter 3 completely receives vascular support 5 in its taut state, tip 10 closes the distal opening of outer catheter 3. It is centered in outer catheter 3 by means of peg 15 formed on tip 10. In order, for example, to close the distal opening of outer catheter 3, tip 10 can fill it completely. In the design examples, shown, it features shoulder 12, which overlaps the outer catheter for sealing purposes. When outer catheter 3 is advanced, its distal edge strikes shoulder 12. Outer catheter 3 is thereby reliably sealed and the physician has a means to detect when the vascular support has been completely folded back. At the location of shoulder 12, the diameter of the tip is essentially equal to the diameter of outer catheter 3. As a result, the edge of the distal outer catheter opening cannot get stuck when catheter 2 is inserted into vessel 1 or while passing narrow points in vessel 1.

Tip 10 is tapered at its distal end and, distally from shoulder 12, is designed conically like an arrowhead with the passage for guide wire 9 arranged in the center and emerging at the tip of the cone. When it closes outer catheter 3, tip 10 extends distally to such an extent that when catheter 2 is advanced, injuries to the vascular wall by outer catheter 3 are prevented. In the case of tip 10 shown in the drawings, the tip extends so far that the entire outer diameter of catheter 2 cannot hit vascular wall 1 at an oblique angle. In this way, catheter 2 is conducted reliably along the longitudinal axis of the vessel and can be advanced without resistance. In this case, guide wire 9, on which tip 10 rides, prevents injury to the vascular wall by means of the conical tip provided on tip 10.

Tip 10 can be made, for example, of a radiologically detectable material. FIG. 3 shows an example of a design in which X-ray-opaque ring 13 is attached to tip 10. Tip 10 need not be X-ray-opaque in that case. Ring 13 is pushed onto stop 14 formed on peg 15. This stop 14 also serves for anchoring the mesh fibers on tip 10. Fibers 6 are connected to ring 13 by means of bonding agents, soldering, or welding.

For use, vascular support 5 is initially located in the taut state at the distal end within outer catheter shaft 3 in catheter 2. Inner catheter 4 is drawn back with respect to outer catheter shaft 3 and vascular support 5 lies against the inner wall of outer catheter shaft 3, as in FIG. 2. The inner catheter is drawn back so far that the distal end of vascular support 5 is also located within outer catheter shaft 3. Tip 10 now closes the distal opening of outer catheter 3 and, if required, serves as a dilator, an expander, in order, for example, to widen the puncture site or a narrow point in the vessel.

In this state, catheter 2 is inserted and fed into vessel 1. When the distal end of catheter 2 has passed the treatment site, outer catheter shaft 2 is drawn back with respect to inner catheter 4, which is held stationary. As a result of connecting vascular support 5 to stationary inner catheter 4, a relative movement between the vascular support and the outer catheter shaft 3 takes place. As a result, vascular support 5 is slowly released, bit by bit, starting from its distal end. It emerges from the distal end of outer catheter shaft 3 and slowly expands into its relaxed state, in which it rests against the vascular wall and supports it. The vascular support is now released as far as required, e.g., until connection point 8 has emerged from the distal end of outer catheter shaft 3, as in FIG. 1.

If vascular support 5 is to be removed from the vessel 1, then outer catheter shaft 3 need only be advanced again with respect to inner catheter 4. By connecting vascular support 5 with inner catheter 4, this again results in a relative movement between the vascular support and outer catheter shaft 3. As a result of connecting vascular support 5 to inner catheter 4 by means of mesh cone 7, the tip of which is fastened to inner catheter 4, catheter shaft 3 will slide on the outside along the mesh of vascular support 5 and will thereby force mesh cone 7, which increases from inner catheter 4, and vascular support 5, which is connected to it, back into their taut form, in which they can again be received by catheter shaft 3. As soon as the vascular support has separated from the vascular wall, inner catheter 4 can also be withdrawn with respect to outer catheter shaft 3. In this way, vascular support 5 can again be drawn back completely into outer catheter shaft 3 and catheter 2 can be removed from vessel 1, or catheter 2 can be moved and vascular support 5 can be brought out again at a corrected site.

An advantageous process for producing catheter 2 according to the invention consists of holding together the converging ends of the two mesh cones 7 and 11 of vascular support 5, in each case by means of a shrunk tube onto the outer diameter of the corresponding anchoring base on inner catheter 4 and tip 10, respectively, while mesh cones 7 and 11 are connected to inner catheter 3 and tip 10, respectively. The shrunk-on tube, in its raw state in which it still has a large diameter, is drawn over vascular support 5. The shrunk-on tube is then heated, as a result of which it shrinks, and thereby also constricts vascular support 5, which it encloses. The dimensions and material of the shrunk-on tube and the heat supplied to the shrunk-on tube can be selected in such a way that the shrunk-on tube constricts vascular support 5 onto the outer diameter of inner catheter 4 or the outer diameter of stop 14 and holds them together there. In this condition, vascular support 5 can then be sealed to inner catheter 4, or a previously applied layer of bonding agent or a layer of bonding agent moving by capillary action under the shrunk-on tube into connection point 8 can be allowed to harden. After this process, the shrunk-on tube can be removed, so that, as shown in FIGS. 1 and 2, a smooth connection point 8 remains behind, which, depending on the process selected, can have essentially the diameter of inner catheter 4.

We claim:

1. A process for making a device with a radially self-expanding permeable mesh vascular support, the process comprising:

(a) providing a tubular outer catheter having a proximal end and a distal end defining a first lumen with a distal opening;

(b) providing an inner catheter having a proximal portion and a distal portion defining a second, guidewire receiving lumen;

(c) providing a vascular support means formed from a radially self-expanding permeable mesh of braided fibers and having a proximal portion and a distal portion;

(d) providing a tapered tip with a proximal portion;

(e) placing the proximal portion of the vascular support means on the distal portion of the inner catheter;

(f) placing a first heat shrink tube over the proximal portion of the vascular support means;

(g) placing the distal portion of the vascular support means on the proximal portion of the tip;

(h) placing a second heat shrink tube over the distal portion of the vascular support means;

(i) heating the first and second heat shrink tubes to simultaneously compress and affix the proximal portion of the vascular support means to the distal portion of the inner catheter and to simultaneously compress and affix the distal portion of the vascular support means to the proximal portion of the tip, such that the vascular support means forms a proximal mesh cone at the proximal portion of the vascular support means and a distal mesh cone at the distal portion of the vascular support means; and (j) disposing the tubular outer catheter about the inner catheter such that the inner catheter is coaxially disposed in the first lumen of the tubular outer catheter and axially movable with respect to the tubular outer catheter, and the tip is adapted to close and seal the distal opening of the outer catheter when the distal opening of the outer catheter is adjacent the proximal portion of the tip.

2. A method for making a medical device comprising:

(a) providing a tubular outer catheter having a proximal end and a distal end defining a first lumen with a distal opening;

(b) providing an inner catheter having a proximal portion and a distal portion defining a second, guidewire receiving lumen;

(c) providing a vascular support means formed from a radially self-expanding permeable mesh of braided fibers and having a proximal portion and a distal portion;

(d) providing a tapered tip with a proximal portion;

(e) attaching the vascular support means to the inner catheter distal portion and tip proximal portion, thereby forming a medical device with a vascular support adapted to self-expand and support vasculature and having a proximal mesh cone at the proximal end of the vascular support means and a distal mesh cone at the distal end of the vascular support means; and (f) disposing the tubular outer catheter about the inner catheter such that the inner catheter is coaxially disposed in the first lumen of the tubular outer catheter and axially movable with respect to the tubular outer catheter, and the tip is adapted to close and seal the distal opening of the outer catheter when the distal opening of the outer catheter is adjacent the proximal portion of the tip.

* * * * *